(12) United States Patent
Guglieri et al.

(10) Patent No.: US 8,981,148 B2
(45) Date of Patent: Mar. 17, 2015

(54) ESTERAMIDE COMPOUNDS, METHODS FOR PREPARING SAME, AND USES THEREOF

(75) Inventors: Massimo Guglieri, Sao Paulo (BR); Thierry Vidal, Lyons (FR)

(73) Assignee: Rhodia Operations, Aubervilliers (FR)

( * ) Notice: Subject to any disclaimer, the term of this patent is extended or adjusted under 35 U.S.C. 154(b) by 167 days.

(21) Appl. No.: 13/635,659

(22) PCT Filed: Mar. 17, 2011

(86) PCT No.: PCT/EP2011/054022
§ 371 (c)(1),
(2), (4) Date: Apr. 30, 2013

(87) PCT Pub. No.: WO2011/113886
PCT Pub. Date: Sep. 22, 2011

(65) Prior Publication Data
US 2013/0210634 A1    Aug. 15, 2013

(30) Foreign Application Priority Data
Mar. 18, 2010 (FR) ..................... 10 51936

(51) Int. Cl.
C07C 233/02 (2006.01)
C07C 231/02 (2006.01)
C07C 235/74 (2006.01)
A01N 25/02 (2006.01)

(52) U.S. Cl.
CPC ............. C07C 233/02 (2013.01); C07C 231/02 (2013.01); C07C 235/74 (2013.01); A01N 25/02 (2013.01)
USPC ............... 564/135; 564/138; 564/199; 71/27; 106/31.13; 106/287.25; 106/505; 504/189; 504/339; 504/342; 510/162; 510/170; 510/176; 510/212; 514/557; 514/561; 514/625; 562/400

(58) Field of Classification Search
CPC .... A01N 25/02; C07C 231/02; C07C 235/74; C08K 5/0016; C08K 5/20; C07D 2300/32; C09D 11/033; C11D 3/32; C11D 3/43; C11D 7/3263; C11D 7/50; C11D 7/5013
USPC .......... 514/557, 561, 625; 504/189, 339, 342; 562/512, 538, 400; 564/135, 138, 199; 510/162, 170, 176, 212; 106/31.13, 106/287.25, 505; 71/27
See application file for complete search history.

(56) References Cited

U.S. PATENT DOCUMENTS

| | | | | |
|---|---|---|---|---|
| 6,054,552 | A * | 4/2000 | Lohmeijer et al. | 528/332 |
| 8,735,324 | B2 * | 5/2014 | Jentzer et al. | 504/358 |
| 2009/0054520 | A1 | 2/2009 | Surburg et al. | |
| 2011/0166025 | A1 | 7/2011 | Jentzer et al. | |
| 2013/0210933 | A1 * | 8/2013 | Guglieri et al. | 514/785 |
| 2013/0211129 | A1 * | 8/2013 | Vidal et al. | 560/155 |
| 2013/0237722 | A1 * | 9/2013 | Vidal et al. | 560/155 |

FOREIGN PATENT DOCUMENTS

| | | | | |
|---|---|---|---|---|
| EP | 0074071 | A1 | 3/1983 | |
| EP | 0411466 | B1 | 2/1991 | |
| EP | 0411466 | B1 * | 12/1995 | ............... G03C 8/40 |
| EP | 2033688 | A2 | 3/2009 | |
| WO | 2009/092795 | A1 | 7/2009 | |
| WO | 2010/130696 | A1 | 11/2010 | |

OTHER PUBLICATIONS

Jerry March, Advanced Organic Chemistry, 1992, John Wiley & Sons, New York, NY; 4th Ed., p. 397.*

Naumov et al., "Esters of N,N-diethyloxamic acid," Zhurnal Organicheskoi Khimii (Journal of Organic Chemistry), 1976, pp. 2507-2511, vol. 12, No. 12, USSR, Abstract only.

International Search Report issued on May 6, 2011, by the European Patent Office as the International Searching Authority in International Patent Application No. PCT/EP2011/054022, and an English language translation of the Search Report.

* cited by examiner

*Primary Examiner* — Jane C Oswecki
(74) *Attorney, Agent, or Firm* — Dentons US LLP

(57) ABSTRACT

An esteramide compound of the following formula (I):

$$R^1OOC\text{-}A\text{-}CONR^2R^3 \qquad (I)$$

is described, wherein:
  A is a covalent bond or a methylene group —$CH_2$—;
  $R^1$ is an optionally substituted, saturated or unsaturated aliphatic or cycloaliphatic hydrocarbon group including from 5 to 36 carbon atoms,
  $R^2$ and $R^3$, either identical or different, are groups selected from a hydrogen atom, and optionally substituted hydrocarbon groups, preferably including from 1 to 36 carbon atoms, and
  $R^2$ and $R^3$ not being simultaneously hydrogen atoms.

Also described, are applications for using the esteramide compound, notably as a solvent.

17 Claims, No Drawings

ESTERAMIDE COMPOUNDS, METHODS FOR PREPARING SAME, AND USES THEREOF

CROSS-REFERENCE TO PRIOR APPLICATIONS

This application is a National Stage of PCT/EP2011/054022, filed Mar. 17, 2011, and designating the United States (published in French on Sep. 22, 2011, as WO 2011/113886 A1; the title and abstract were published in English), which claims priority to FR 10 51936, filed Mar. 18, 2010, each hereby expressly incorporated by reference in its entirety and each assigned to the assignee hereof.

The present invention relates to compounds of the esteramide type, notably of the oxalic or malonic esteramide type, as well as to the method for preparing said compounds.

It also relates to the uses of these compounds, notably as a solvent.

Industry uses many chemical compounds as solvents, for example for preparing chemicals and materials, for formulating chemical compounds or for treating surfaces. For example, solvents are used for formulating plant protection actives notably in the form of emulsifiable concentrates (EC) intended to be diluted in water by the farmer, before application on a field.

Industry is searching for novel compounds allowing variation and optimization of the products and methods in which solvents, notably polar or slightly polar solvents are to be used. Industry notably needs compounds of modest cost having interesting properties of use. Industry also needs compounds having a toxicological and/or ecological profile perceived as being favorable, notably low volatility (low VOC), good biodegradability, low toxicity and/or low hazardousness.

The use of dialkylamides as solvents is known. These are products of formula R—CONMe$_2$, wherein R is a hydrocarbon group like a typically C$_6$-C$_{30}$ alkyl group. Such products are notably marketed under the name of Genagen® by Clariant. These solvents notably find applications in the plant protection field.

Diesters of dicarboxylic acids are also known as solvents, notably diesters obtained by esterification of a mixture of adipic acid, glutaric acid and succinic acid. Such products are notably marketed under the names of Rhodiasolv® RPDE, Rhodiasolv® IRIS and Rhodiasolv® DIB by Rhodia.

There remains a need, as explained above for novel solvents, notably in plant protection formulations, and for novel compounds.

The object of the present invention is therefore to provide novel solvents, particularly suitable for plant protection applications, having specific properties allowing them to be used as a solvent, notably improved properties. In terms of preparation of emulsifiable concentrates and other formulations of plant protection actives.

Thus, the present invention relates to esteramide compounds of the following formula (I):

wherein:
- A is a covalent bond or a methylene group —CH$_2$—,
- R$^1$ is a saturated or unsaturated, aliphatic or cycloaliphatic optionally substituted hydrocarbon group, comprising from 5 to 36 carbon atoms,
- R$^2$ and R$^3$, either identical or different, are groups selected from hydrogen and hydrocarbon groups, optionally substituted, preferably comprising from 1 to 36 carbon atoms, R$^2$ and R$^3$ not being simultaneously hydrogens, In formula (I), R$^1$ represents a hydrocarbon group having from 5 to 36 carbon atoms, optionally substituted, which may be a linear or branched, saturated or unsaturated acyclic aliphatic group or a saturated or unsaturated carbocyclic group.

Preferentially, R$^1$ represents a linear or branched, saturated or unsaturated acyclic aliphatic group, preferably having from 5 to 36 carbon atoms.

The invention does not exclude the presence of an unsaturation on the hydrocarbon chain such as one or, several double bonds which may either be conjugate or not, or else a triple bond.

The hydrocarbon chain may optionally be interrupted by a heteroatom (for example oxygen, nitrogen or sulfur) or a functional group (carbonyl group) or bearing one or several substituents (for example formyl) insofar that the latter are not a nuisance as regards the reaction conditions or the contemplated application.

As preferred examples for R$^1$, mention may be made of alkyl groups having from 5 to 20 carbon atoms, and more preferentially from 5 to 15 carbon atoms.

In formula (I), R$^1$ may also represent a monocyclic, carbocyclic group. The number of carbon atoms in the ring may widely vary from 5 to 8 carbon atoms but is preferably equal to 5 or 6 carbon atoms.

The carbocycle may be saturated or comprise 1 or 2 unsaturations in the ring, preferably 1 to 2 double bonds.

As preferred examples of carbocyclic and monocyclic groups for R$^1$, mention may be made of cyclopentyl, cyclohexyl, cyclohexenyl or cyclopentadienyl groups.

In formula (I), R$^2$ and R$^3$ may represent a hydrocarbon group having from 1 to 36 carbon atoms, optionally substituted, which may be a linear or branched, saturated or unsaturated acyclic aliphatic group; a monocyclic or polycyclic, saturated, unsaturated or aromatic, carbocyclic or heterocyclic group; an aliphatic and/or carbocyclic and/or heterocyclic sequence of groups, as defined earlier.

Preferentially, R$^2$ and R$^3$ represent a linear or branched saturated acyclic aliphatic group preferably having from 1 to 36 carbon atoms.

The invention does not exclude the presence of an unsaturation on the hydrocarbon chain such as one or several double bonds which may either be conjugate or not, or else a triple bond.

The hydrocarbon chain may optionally be interrupted by a heteroatom (for example oxygen or sulfur) or a functional group (for example a carbonyl group CO) or bearing one or several substituents (for example formyl —CHO) insofar that the latter are not a nuisance as regards the reaction conditions or the contemplated application.

As preferred examples for R$^2$ and R$^3$, mention may be made of alkyl groups having from 1 to 20 carbon atoms, and more preferentially from 1 to 10 carbon atoms.

In formula (I), R$^2$ and R$^3$ may also represent a monocyclic, carbocyclic group. The number of carbon atoms in the ring may widely vary from 5 to 8 carbon atoms but is preferably equal to 5 or 6 carbon atoms.

The carbocycle may be saturated or comprise 1 or 2 unsaturations in the ring, preferably 1 to 2 double bonds.

As preferred examples of carbocyclic and monocyclic groups for R$^2$ and R$^3$, mention may be made of cyclopentyl, cyclohexyl, cyclohexenyl or cyclopentadienyl groups.

R$^2$ and R$^3$ may also represent a polycyclic hydrocarbon group formed by at least two saturated and/or unsaturated carbocycles or by at least two carbocycles, only one of which is aromatic, and forming together ortho-fused or ortho- and perk fused systems. Generally, the rings are C$_3$-C$_8$, preferably $C_6$ rings. As more particular examples, mention may be made of the bornyl group or of the tetrahydronaphthalene group.

$R^2$ and $R^3$ may also represent a monocyclic aromatic carbocyclic group having 6 to 10 carbon atoms, preferably a phenyl group.

$R^2$ and $R^3$ may also represent a polycyclic aromatic carbocyclic group having from 8 to 12 carbon atoms, the cycles may form together ortho-fused, ortho- and peri-fused systems. Mention may more particularly be made of a naphthyl group.

In the case when $R^2$ and $R^3$ represent a saturated or unsaturated monocyclic carbocyclic group, it is possible that one or several of the carbon atoms of the ring be replaced with a heteroatom, preferably an oxygen, nitrogen or sulfur atom or by a functional group, preferably a carbonyl or ester, thus leading to a monocyclic heterocyclic compound. The number of atoms in the ring may widely vary from 5 to 8 but is preferably equal to 5 or 6, like for example when the formed ring is a pyrrolidine, piperidine, morpholine or piperazine ring.

$R^2$ and $R^3$ may also represent a polycyclic aromatic heterocyclic group defined as either being a group formed by at least two aromatic heterocycles or not containing at least one heteroatom in each ring and forming together ortho-fused or ortho- and peri-fused systems or either a group formed by at least one aromatic hydrocarbon cycle or not and at least one aromatic heterocycle not forming together ortho-fused or ortho- and peri-fused systems.

As examples of groups of the heterocyclic type, mention may be made inter alia of furyl, thienyl, isoxazolyl, furazanyl, isothiazolyl, pyridyl, pyridazinyl, pyrimidinyl, pyranyl groups and quinolyl, naphthyridinyl, benzopyranyl and benzofuranyl groups.

In formula (I), $R^2$ and $R^3$ may also represent a sequence of aliphatic and/or carbocyclic and/or heterocyclic groups.

Thus, a linear or branched, saturated or unsaturated, acyclic aliphatic group may optionally bear a cyclic substituent. By ring, is meant a saturated, unsaturated or aromatic, carbocyclic or heterocyclic ring.

The acyclic aliphatic group may be connected to the ring through a valency bond, a heteroatom or a functional group such as oxy, carbonyl, carboxy or sulfonyl.

As examples of cyclic substituents, it is possible to envision cycloaliphatic, aromatic or heterocyclic, notably cycloaliphatic substituents, comprising 6 carbon atoms in the ring or benzene substituents, these cyclic substituents being themselves optionally bearers of substituent(s). In particular, mention may be made of alkyl or alkoxy groups having from 1 to 4 carbon atoms.

Among the aliphatic groups bearing a cyclic substituent, arylalkyl groups having from 7 to 12 carbon atoms, notably benzyl or phenylethyl groups, are more particularly envisioned.

When the groups $R^2$ and $R^3$ comprise more than one cyclic ring (carbocycle or heterocycle), the cyclic rings may be fused (o- or peri-fused) pairwise or attached pairwise by σ bonds. As examples, mention may be made of a biphenyl group It should be noted that if the groups $R^1$, $R^2$ and $R^3$ comprise any ring, it is possible that this ring bear a substituent. The nature of the substituent is arbitrary insofar that it does not interfere at the level of the desired product. The substituents most often borne by the ring are one or several alkyl or alkoxy groups preferably having from 1 to 4 carbon atoms, preferentially methyl, tert-butyl or methoxy, and functional groups more particularly, amino, hydroxyl, halogen, perfluoroalkyl (preferably trifluoromethyl), nitrile, (di)alkylamino, carboxy, carboxyalkyl or ester (preferably a lower $C_1$-$C_4$ alkyl).

The "alkoxy" groups according to the present invention are groups of formula —O-alkyl, the alkyl group being as defined earlier.

The term of "alkylamino" refers to a —NH-alkyl group, the alkyl group being as defined above. The term of "dialkylamino" refers to a —N(alkyl)$_2$ group, the alkyl group being as defined above.

The term of "carboxyalkyl" refers to a HOOC-alkyl-group, the alkyl group being as defined above, as an example of carboxyalkyl groups, mention may notably be made of carboxymethyl or carboxyethyl.

According to a particularly advantageous embodiment, the present invention relates to esteramide compounds of the following formula (I'):

wherein:

A is a covalent bond or a methylene group —CH$_2$—, $R^1$ is an optionally substituted, linear or branched, saturated or unsaturated acyclic aliphatic group comprising from 5 to 36 carbon atoms, The compounds of formula (I') correspond to the compounds of formula (I) wherein $R^2$=$R^3$=Me.

The compounds of formula (I') are particularly advantageous. Indeed, unlike the compounds of formula (I) with one of $R^2$ and $R^3$ representing H which have some acidity, the compounds of formula (I') do not have such acidity and thus in the case of a combination with pesticides, the latter will not interact with said pesticides.

The preferred compounds, object of the present invention, fit formula (I) wherein A is a covalent bond.

Preferably in formula (I'), A represents a covalent bond.

According to a particularly advantageous embodiment of the present invention, in the aforementioned formula (I'), $R^1$ is selected from linear or branched optionally substituted alkyl groups, comprising from 5 to 36 carbon atoms and cycloalkyl groups.

According to a particularly advantageous embodiment of the present invention, in the aforementioned formula (I'), $R^1$ is selected from linear or branched optionally substituted alkyl groups, comprising from 5 to 36 carbon atoms.

Preferentially, in the aforementioned formula (I'), $R^1$ is selected from linear or branched optionally substituted alkyl groups, comprising from 5 to 15 carbon atoms.

Preferably, among these linear or branched alkyl groups, mention may be made of n-pentyl, isopentyl, sec-pentyl, n-hexyl, isohexyl, sec-hexyl, methylcyclohexyl, 2-ethylbutyl, 3-methylpentyl, n-heptyl, isoheptyl, sec-heptyl, 3-methylhexyl, 4-methylhexyl, 1-ethylpentyl, 2-ethylpentyl, 3-ethylpentyl, n-octyl, isooctyl, 3-methylheptyl, n-nonyl, n-decyl, undecyl, n-dodecyl, tridecyl, tetradecyl and pentadecyl groups.

As examples of cycloalkyl groups, mention may be made of the cyclopentyl group and the cyclohexyl.group.

As for preferred meanings of $R^2$ and $R^3$, the $R^2$ et $R^3$ groups are groups, either identical or different, selected from alkyl, alkenyl, cycloalkyl, aryl and arylalkyl groups, said groups may optionally be substituted.

According to the present invention, the "alkyl" groups represent saturated linear or branched chain hydrocarbon groups, comprising from 1 to 36 carbon atoms, preferably from 1 to 20 carbon atoms and even more preferentially from 1 to 15 carbon atoms (they may be typically represented by the formula $C_n$—$H_{2n+1}$, n being an integer representing the number of carbon atoms).

Mention may notably be made, when they are linear, of methyl, ethyl, propyl, butyl, pentyl, hexyl, heptyl, octyl, nonyl, decyl, undecyl, dodecyl, tridecyl, tetradecyl and pentadecyl groups. Mention may notably be made when they are branched or substituted with one or several alkyl groups, of isopropyl, isobutyl, tert-butyl, sec-butyl, isopentyl, sec-pentyl, isohexyl, sec-hexyl, 2-ethylbutyl, 3-methylpentyl, isoheptyl, sec-heptyl, 3-methylhexyl, 4-methylhexyl, 1-ethylpentyl, 2-ethylpentyl, 3-ethylpentyl, isooctyl, and 3-methylheptyl groups.

Among the alkenyl groups, mention may also be made of groups comprising at least one unsaturation in their carbon chain. As an example, mention may be made of the group —$CH_2$—CH=$CH_2$ or —C($CH_3$)=$CH_2$.

By "cycloalkyl" group, is more particularly envisioned a monocyclic carbocyclic group having from 5 to 8 carbon atoms, and preferably 5 or 6 carbon atoms. Preferentially, mention may be made of the cyclopentyl or cyclohexyl group.

The term of "aryl" refers to a mono- or bi-cyclic hydrocarbon aromatic system comprising from 6 to 30, preferably from 6 to 10 carbon atoms. Among aryl groups, mention may notably be made of the phenyl group.

When an alkyl group is substituted with an aryl group, this is referred to as an "arylalkyl" or "arylalkyl" group. <<Arylalkyl>> or <<arylalkyl>> groups are aryl-alkyl- groups, the aryl and alkyl groups being as defined above. Among arylalkyl groups, mention may notably be made of the benzyl or phenethyl group.

The aforementioned "alkyl", "aryl" and "cycloalkyl" groups may be substituted with one or several substituents. Among these substituents, mention may be made of the following groups: amino, hydroxy, halogen, alkyl, alkoxy, (di)alkylamino, perfluoroalkyl (preferably trifluoromethyl).

The "alkoxy" groups according to the present invention are groups of formula —O-alkyl, the alkyl group being as defined earlier.

The term of "alkylamino" refers to a —NH-alkyl group, the alkyl group being as defined above. The term of "dialkylamino" designates a —N(alkyl)$_2$ group, the alkyl group being as defined above.

Among halogen atoms, more particularly, mention is made of fluorine, chlorine, bromine and iodine atoms.

Among preferred compounds of the invention, mention may be made in particular of the compounds of formula (I), wherein $R^2$ and $R^3$, either identical or different, are selected from methyl, ethyl, n-propyl, isopropyl, n-butyl, isobutyl, tertiobutyl, n-pentyl, isoamyl, n-hexyl, cyclohexyl and hydroxyethyl, —$CH_2$—CHO, —$COCH_3$ et —$CH_2COCH_3$ groups.

According to a particularly advantageous embodiment, the present invention relates to esteramide compounds of the following formula (I"):

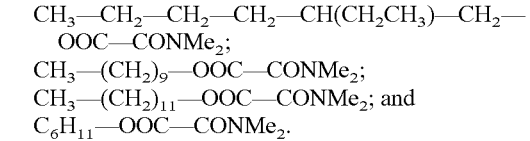

wherein $R^1$ is, as defined above in formula (I').

Among the preferred compounds of the present invention fitting formula (I), mention may notably be made of the following compounds:

$CH_3$—$CH_2$—$CH_2$—$CH_2$—CH($CH_2CH_3$)—$CH_2$—OOC—$CONMe_2$;
$CH_3$—($CH_2$)$_9$—OOC—$CONMe_2$;
$CH_3$—($CH_2$)$_{11}$—OOC—$CONMe_2$;
$C_6H_{11}$—OOC—$CONMe_2$;
$CH_3$—$CH_2$—$CH_2$—$CH_2$—CH($CH_2CH_3$)—$CH_2$—OOC—$CONEt_2$;
$CH_3$—($CH_2$)$_9$—OOC—$CONEt_2$;
$CH_3$—($CH_2$)$_{11}$—OOC—$CONEt_2$ and
$C_6H_{11}$—OOC—$CONEt_2$.

Among the preferred compounds of the present invention fitting formula (I'), mention may notably be made of the following compounds:

$CH_3$—$CH_2$—$CH_2$—$CH_2$—CH($CH_2CH_3$)—$CH_2$—OOC—$CONMe_2$;
$CH_3$—($CH_2$)$_9$—OOC—$CONMe_2$;
$CH_3$—($CH_2$)$_{11}$—OOC—$CONMe_2$; and
$C_6H_{11}$—OOC—$CONMe_2$.

Preferably, the compounds applied within the scope of the present invention have a melting point of less than or equal to 40° C., preferably 20° C.

The compounds of the invention have specific properties and are particularly performing in terms of preparation of plant protection formulations of the plant protection active emulsifiable concentrate type.

Method

The present invention also relates to a method for preparing an esteramide compound of formula (I) as defined above, comprising the following steps:

a) reacting a compound of formula (II) ROOC-A-COOR, R being a methyl group or an ethyl group, with an amine of formula $HNR^2R^3$, $R^2$ and $R^3$ being as defined above in formula (I), in the presence of a basic catalyst, in order to obtain a compound of the following formula (III): ROOC-A-CONR$^2$R$^3$; and b) reacting the compound of the aforementioned formula (III) with an alcohol of formula $R^1$OH, $R^1$ being as defined above in formula (I), in the presence of a catalyst, in order to obtain the compound of formula (I).

The present invention also relates to a method for preparing an esteramide compound of formula (I'), as defined above, comprising the following steps:

a) reacting a compound of formula (II) ROOC-A-COOR, R being a methyl group or an ethyl group, with an amine of formula $HNMe_2$, in the presence of a basic catalyst, in order to obtain a compound of the following formula (III'): ROOC-A-CONMe$_2$; and b) reacting the compound of the aforementioned formula (III') with an alcohol of formula $R^1$OH, $R^1$ being as defined above in formula (I'), in the presence of a catalyst, in order to obtain the compound of formula (I').

The present invention also relates to a method for preparing an esteramide compound of formula (I), as defined above, comprising the following steps:

a') reacting a compound of formula (II) ROOC-A-COOR, R being a methyl group or an ethyl group, with an alcohol of formula $R^1$OH, $R^1$ being as defined above in formula (I), in the presence of a catalyst, in order to obtain a mixture consisting of the compound of the following formula (IV): $R^1$OOC-A-COOR and of the compound of the following formula (V): $R^1$OOC-A-COOR$^1$; and b') reacting the aforementioned mixture as obtained in the preceding step a') with an amine of formula $HNR^2R^3$, $R^2$ and $R^3$ being as defined above in formula (I), in the presence of a basic catalyst, in order to obtain the compound of formula (I).

Another method for preparing a compound of formula (I') as defined above comprises the following steps:

a') reacting a compound of formula (II) ROOC-A-COOR, R being a methyl group or an ethyl group, with an alcohol of formula $R^1$OH, $R^1$ being as defined above in formula (I'), in the presence of a catalyst, in order to obtain a mixture consisting of the compound of the following formula (IV'): $R^1$OOC-A-COOR and of the compound of the following formula (V'): $R^1$OOC-A-COOR$^1$; and b') reacting the aforementioned mixture as obtained in the preceding step a') with an amine of formula $HNMe_2$, in the presence of a basic catalyst, in order to obtain the compound of formula (I').

The present invention also relates to a method for preparing an esteramide compound of formula (I), as defined above, comprising the following steps:

a") reacting a compound of formula (II) ROOC-A-COOR, R being a methyl group or an ethyl group, with an alcohol of formula $R^1OH$, $R^1$ being as defined above in formula (I), in the presence of an acid catalyst, in order to obtain a mixture consisting of the compound of the following formula (IV): $R^1OOC$-A-COOR and of the compound of the following formula (V): $R^1OOC$-A-COOR$^1$; and b") reacting the aforementioned mixture as obtained in the preceding step a') with an amine of formula $HNR^2R^3$, $R^2$ and $R^3$ being as defined above in formula (I), in the presence of a basic catalyst, in order to obtain the compound of formula (I).

Another method for preparing a compound of formula (I') as defined above, comprises the following steps:

a''') reacting a compound of formula (II) ROOC-A-COOR, R being a hydrogen or a methyl group or an ethyl group, with an alcohol of formula $R^1OH$, $R^1$ being as defined above in formula (I'), in the presence of an acid catalyst, in order to obtain a mixture consisting of the compound of the following formula (IV'): $R^1OOC$-A-COOR and of the compound of the following formula (V'): $R^1OOC$-A-COOR$^1$; and b") reacting the aforementioned mixture as obtained in the preceding step a') with an amine of formula $HNMe_2$, in the presence of a basic catalyst, in order to obtain the compound of formula (I').

Among the basic catalysts which may be applied in steps a), b') and b") mention may notably be made of sodium methylate (NaOMe), sodium (Na), potassium carbonate ($K_2CO_3$), sodium carbonate ($Na_2CO_3$), sodium hydride (HNa), sodium amide ($NH_2Na$) or basic solid supports such as basic resins, aluminas.

For applying steps b) and a'), it is possible to equally use a basic catalyst or an acid catalyst.

Among acid catalysts, mention may notably be made of Lewis or Brönsted acids and more particularly sulfuric acid ($H_2SO_4$) or titanium tetrabutoxide (IV) (Ti(OBu)$_4$), acid resins (for example sulfonic resins), boron trifluoride etherate ($BF_3OEt2$), aluminum chloride ($AlCl_3$), zinc chloride ($ZnCl_2$), rare earth derivatives such as lanthanum chloride ($LaCl_3$), tin chloride ($SnCl_2$), bismuth chloride ($BiCl_3$), or dibutyltin acetate ($Bu_2SnOAc$).

As regards basic catalysts, they are also selected from the catalysts mentioned above for steps a), b') and b").

For all the steps of the method of the invention, it is also possible to use a catalyst which is a supported enzyme of the amidase or liphase type, such enzymes being commercially available.

Steps a), b') and b") of the method of the invention are advantageously conducted at a temperature comprised between 20 and 150° C., preferably between 20 and 100° C. and notably between 20 and 50° C. The pressure is generally comprised between 1 and 5 bars.

Steps a'), a") and b) of the method of the invention are advantageously conducted at a temperature comprised between 20 and 180° C., preferably between 60 and 160° C. and notably between 100 and 150° C. The pressure is generally close to atmospheric pressure.

Steps a), a'), a"), b), b') and b") are advantageously conducted under an inert gas atmosphere, preferably with nitrogen inertization.

The concentration conditions of the reagents introduced into the method of the invention are advantageously selected so that the reaction medium is homogeneous, while limiting the dilution of the reaction medium for ecological and economical reasons.

The products from the method of the invention are recovered according to standard methods known to one skilled in the art, such as for example by means of a distillation, filtration or extraction step.

The compound of formula (II) ROOC-A-COOR, R being a methyl or ethyl, is prepared by reaction of oxalic acid HOOC—COOH with methanol or ethanol respectively, preferably in the presence of an acid catalyst such as sulfuric acid and while removing the water formed during the reaction.

Uses

The present invention also relates to use of the compounds of formula (I) or (I') defined above, as a solvent, co-solvent, coalescence agent, crystallization inhibitor, plasticizer or agent for increasing biological activity.

In the present application, the term of solvent is meant, broadly speaking, to notably cover the functions of a co-solvent, of a crystallization inhibitor, of a stripping agent. The term of solvent may notably refer to a liquid product at the temperature of use, preferably with a melting point of less than or equal to 40° C., preferably 20° C., which may contribute to making the solid material liquid, to making a viscous liquid more fluid or to preventing or delaying the solidification or crystallization of material in a liquid medium.

By co-solvent, is meant that other solvents may be associated with it.

The use of a solvent or as a co-solvent notably comprises the use for dissolving a compound in a formulation, in a reaction medium, the use for totally or partly solubilizing a product to be removed (degreasing, stripping), and/or for facilitating detachment of films of materials.

By agent for increasing biological activity is meant a compound which combined with a molecule having biological activity, will allow an increase in the biological activity of said molecule (by synergy for example).

In the present application, a "compound of the invention" refers to any compound fitting the general formula (I) or (I'). It is mentioned that the term of "compound" also covers mixtures of several molecules fitting the general formula (I) or (I'). Therefore this may be a molecule of formula (I) or (I') or a mixture of several molecules of formula (I) or (I').

In the present application, by "material composition", is meant a composition, which is more or less complex, comprising several chemical compounds. This may typically be a non-purified or modestly purified reaction product. The compound of the invention may notably be isolated and/or marketed and/or used as a material composition comprising it. If the compound of the invention is a mixture of several compounds of formula (I) then this is also a material composition. The compound of the invention, in the form of a pure molecule or in the form of a mixture fitting formula (I), may be comprised in a material composition.

In the material composition, the compound of the invention may for example represent at least 10% by weight. Preferably, this is the main compound of the material composition. By main compound is meant in the present application, the compound for which the content is the highest, even if its content is less than 50% by weight (for example in a mixture of 40% of A, 30% of B and 30% of C, product A is the main compound). Even more preferably, the compound of the invention represents at least 50% by weight of the material composition, for example from 70% to 95% by weight, and even from 75% to 90% by weight. As indicated above, the material composition may be a reaction product.

The present invention also relates to the use as defined above, wherein the compound of formula (I) or (I') is in a plant protection formulation, in a cleaning formulation, in a stripping formulation, in a degreasing formulation, in a lubricant formulation, in a coating formulation, in a pigment or ink formulation, in a formulation for solubilizing resins, notably PVDF resins (polyvinylidene fluoride powder), in a formulation for cleaning photoresists or further in a formulation for cleaning screens, notably liquid crystal screens (LCD).

The compound may for example be used as a coalescence agent in an aqueous paint formulation.

The compound may notably be used as a resin solvent for example in the cable cladding industry or in the electronics industry, notably as a solvent for PVDF.

The compound may notably be used as a cleaning solvent and/or a stripping solvent in the electronics industry. It may notably be used in lithium batteries. It may notably be used on photoresist resins, polymers, waxes, fats, oils.

The compound may notably be used for cleaning inks, for example during the production of inks or during the use of printing ink.

The compound may notably be used for bleaching paper.

The compound may notably be used for cleaning sieves or other tools applied in methods for making and/or recycling paper.

The compound may notably be used for cleaning bitumens or bituminous sands (tar sands), for example on coated substrates, on tools used for applying these materials, on dirty clothes, on dirty vehicles.

The compound may notably be used for cleaning flying machines such as airplanes, helicopters, space shuttles.

The compound may notably be used as degreasing agent on metal surfaces, for example surfaces of tools, of manufactured objects, of metal sheets, of molds, notably in steel or in aluminium or in alloys of these metals.

The compound may notably be used as a cleaning solvent on hard surfaces or textile surfaces.

The compound may notably be used as a solvent for stripping paint or resins, on tool surfaces, for example foundry molds, on surfaces of industrial sites (floors, partitions, etc.,).

The compound may notably be used as a plasticizer in formulations of thermoplastic polymers.

The cleaning and/or degreasing formulations may notably be formulations for home care, carried out in homes or in public domains (hotels, offices, factories . . . ). These may be formulations for cleaning hard surfaces such as floors, furniture surfaces and surface areas of kitchens and bathrooms, dishes. These formulations may also be used in the industrial sphere for degreasing manufactured products and/or cleaning them.

Within the scope of uses in reaction media, mention is notably made of the uses within the scope of polymerizations in solution, notably for preparation in solution of polycondensates, notably polyimides or polyesters or polyamides or polyamide-imides or polyurethane dispersed in water (PUD), notably partly or totally aromatic polycondensates such as aromatic polyamides (aramides).

The present invention also relates to a plant protection formulation, comprising an esteramide compound of formula (I) as defined above in combination with an active product.

The compound of the invention and/or a material composition comprising it, described above, may notably be used in plant protection formulations comprising a solid active product. More details are given below, where the term of "solvent" may designate the compound of the invention or a material composition comprising it, described above.

The plant protection formulation is generally a concentrated plant protection formulation comprising an active product.

Agriculture uses many active materials (or active products) such as fertilizers or pesticides, for example insecticides, herbicides or fungicides. These are referred to as active plant protection products (or active material products). Active plant protection products are generally produced in a pure or highly concentrated form. They have to be used on farms with low concentrations or used for treating agricultural products after harvesting. For this purpose, they are generally formulated with other ingredients in order to allow easy dilution by the farmer. These are referred to as plant protection formulations. The dilution performed by the farmer is generally carried out by mixing the plant protection formulation with water.

Thus plant protection formulations have to allow easy dilution by the farmer, in order to obtain a product in which the plant protection product is properly dispersed, for example as a solution, emulsion, suspension or suspo-emulsion. Plant protection formulations thus allow transport of a plant protection product in a relatively concentrated form, easy packaging and/or easy handling for the final user. Different types of plant protection formulations may be used depending on the different plant protection products. For example, mention is made of emulsifiable concentrates (EC), concentrated emulsions (emulsion in water EW), microemulsion (ME), wettable powders (WP), water-dispersible granules (WDG). The formulations which may be used depend on the physical form of the plant protection product (for example a solid or liquid), and on its physicochemical properties in the presence of other compounds such as water or solvents.

After dilution by the farmer, for example by mixing with water, the plant protection product may be found in different physical forms: solution, dispersion of solid particles, dispersion of droplets of the product, droplets of solvent in which the product is dissolved . . . . The plant protection formulations generally comprise compounds with which these physical forms may be obtained. These for example may be surfactants, solvents, mineral supports and/or dispersants. Most often, these compounds do not have an active nature, but a nature of a formulation aid ingredient. Plant protection formulations may notably be in liquid form or in solid form.

In order to prepare plant protection formulations of solid active plant protection products, it is known how to solubilize the product in a solvent. The plant protection formulation thus comprises a solution of the product in the solvent. The formulation may be in solid form, for example as a wettable powder (WP) where the solution impregnates an inorganic support, for example kaolin and/or silica. The formulation may alternatively be in liquid form, for example as an emulsifiable concentrate (EC) having a single limpid liquid phase comprising the solvent and the product in solution, which may form an emulsion by addition of water, with stirring or with weak stirring. It may also be in the form of a concentrated emulsion (EW), the dispersed phase of which in water comprises the solvent and the product in solution in the solvent. It may also be in the form of a limpid microemulsion (ME), the dispersed phase of which in water comprises the solvent and the product in solution in the solvent, of a soluble concentrate (SL) having a single limpid liquid phase comprising the solvent and the product in solution, which may form a solution by addition of water, or as a suspo-emulsion (SE), containing at least two dispersed phases, a solid and a liquid phase.

Certain solid plant protection actives are often difficult to formulate. For certain plant protection actives, it is difficult to produce stable, easy-to-dilute concentrated formulations for the farmer, and without any (proven or perceived) substantial drawbacks as regards safety, toxicity and/or ecotoxicity. For certain actives, it is difficult to formulate them at relatively high concentrations with sufficient stability. In particular, it is necessary to avoid the occurrence of crystals in particular at low temperature and/or during the dilution and/or during storage of the diluted composition. The crystals may have negative effects, notably clogging the filters of the devices used for spreading out the diluted composition, clogging the spraying devices, reducing the amount of distributed formulation on the field, generating unnecessary problems, waste streams for removing the crystals, and/or causing poor spreading of the active product over the farm field. For example tebuconazole is a particularly efficient fungicide and of widespread use, for cultivating soya notably which often shows this type of behavior.

The formulations comprising the solvent of the present invention notably have:
  solubilization of large amounts of actives,
  absence of crystallization even under demanding conditions, and/or
  good biological activity which may be due to good solvation.

The plant protection formulation may further be a concentrated plant protection formulation comprising:
  a) an active plant protection product,
  b) the esteramide compound of formula (I) or (I') according to the present invention,
  c) optionally at least one co-solvent or another solvent,
  d) optionally at least one surfactant,
  e) optionally water.

Active and solid plant protection products, notably products which are not soluble in water, are known to one skilled in the art. The active plant protection product may notably be a herbicide, an insecticide, an acaricide, a fungicide, or a rodenticide, for example a raticide.

As examples of insecticides and acaricides which are suitable for the invention, mention may be made of those which belong to the families of:
  organo-halogenated or chlorinated products such as for example D.D.T. (dichloro diphenyl trichloro-ethane), lindane (γ isomer of hexachloro-cyclohexane), chlordane (octachlorotetrahydro methano indene), toxaphene;
  carbinols such as for example dicofol (dichlorophenyl trichloroethanol);
  organophosphorus compounds such as for example bromophos [(4-bromo-2,5-dichloro-phenoxy)-dimethoxy-thioxo-phosphorane), diazinon (O,O-diethyl-O-(2-isopropyl-6-methyl-pyrimidin-4-yl)phosphorothioate), feni-trothion (O,O-dimethyl-O-nitro-4-m-tolylphosphorothioate), malathion (S-1,2-bis(ethoxycarbonyl) ethyl-O,O-dimethyl-phosphorodithioate), parathion (O,O-diethyl-O-nitro-4-phenylphosphorothioate), trichlorfon (dimethyl-2,2,2-trichloro-1-hydroxy-ethylphosphonate), dimethoate (O,O-dimethyl-5-methyl-carbamoylmethyl phosphorodithioate);
  sulfones and sulfonates such as for example tetradifon (tetrachloro diphenylsulfone);
  carbamates such as for example carbaryl (naphthyl N-methylcarbamate), methomyl, ((methylthio ethylidene amine) N-methylcarbamate);
  benzoylureas such as for example diflubenzuron (difluoro benzoyl chlorophenylurea);
  synthetic pyrethrinoids;
  acaricides such as for example cyhexatin (tricyclohexyl-hydroxystannane).

Fungicides which may be applied in the invention may for example be selected from:
  carbamates such as for example benomyl (methyl butylcarbamoyl benzimidazolyl carbamate), carbendazime (methyl benzimidazolyl carbamate), ziram (zinc dimethyl dithiocarbamate), zineb (zinc ethylene-bis dithiocarbamate), maneb (manganese ethylene-bis dithiocarbamate), mancozeb (zinc and manganese ethylene-bis-dithiocarbamate), thiram (bis dimethyl-thiocarbamoyl disulfide);
  benzene derivatives such as for example PCNB (pentachloronitrobenzene);
  phenol derivatives such as for example dinocap ((methylheptyl)dinitrophenyl crotonate);
  quinone such as for example dithianon (dioxodihydro naphtho dithiine dicarbonitrile);
  dicarboximides such as for example captan (trichloromethylthio tetrahydroisoindolinedione), folpel (trichloromethylthio isoindolinedione), iprodione (dichlorophenyl isopropyl carbamoyl dichlorophenyl-hydantoin);
  amines and amides such as for example benodanil (iodobenzanilide), metalaxyl (methyl dimethylphenyl methoxyacetyl alalinate);
  diazines such as for example pyrazophos (ethyl and ethoxycarbonyl methyl pyrazolo pyrimidine thiophosphate), fenarimol (chlorophenyl chlorophenyl pyrimidine methanol);
  sulfamides and sulfur-containing derivatives such as for example dichlofluanide (dichloro fluoro methylthiodimethyl phenyl sulfamide);
  guanidines such as for example doguadine (dodecylguanidine acetate);
  heterocycles such as for example etridiazole (ethoxy trichloromethyl thiadiazole), triadimefon (chlorophenoxy dimethyltriazole butanone);
  metal monoethyl phosphites such as for example phosethyl-Al (aluminium tris-O-ethylphosphonate);
  organostannic compounds such as for example fentin-acetate (triphenyl tin).

As chemical substances having herbicidal properties, it is possible to resort to those which are found in the following chemical formulae:
  phenolic compounds such as for example dinoseb, (dinitrobutylphenol);
  carbamates such as for example phenmedipham (methyl tolylcarbamoyloxyphenyl carbamate);
  substituted ureas such as for example neburon (butyl dichlorophenyl methyl urea), diuron (dichlorophenyl dimethyl urea), linuron (dichlorophenyl methoxymethyl urea);
  diazines such as for example, bromacil (bromobutyl methyl uracil), chloridazone (phenylamino chloropyridazone),
  triazines such as for example, simazine (chloro bis-ethylamino s-triazine), atrazine (chloroethylamino isopropylamino-s-triazine), terbutylazine (chloroethylamino butylamino s-triazine), terbumeton (tert-butylamino ethylamino methoxy triazine), prometryne (methylthio bis isopropylamino s-triazine), ametryne (methylthio ethylamino isopropylamino s-triazine), metribuzin (methylthio butylamino triazine-one), cyanazine (chloro ethylamino s-triazine-ylaminomethyl-propionitrile);

amides such as for example napropamide (naphthoxydiethyl propionamide), propachlor-(isopropyl chloroacetanilide);
quaternary ammoniums;
benzonitriles;
toluidines such as for example ethalfluraline (dinitro-ethylmethyl propenyl trifluoro methylaniline), oryzalin (dinitrodipropyl sulfanil-amide);
triazoles;
various derivatives such as for example benazolin (chloro oxo benzothiazoline acetic acid), dimefuron (chloro oxo tert-butyl oxadiazoline phenyl dimethyl urea), bromophenoxime (dibromo hydroxy dinitro phenyl benzaldoxime), pyridate (octyl chlorophenylpyridazinylcarbothiolate).

Like other examples of biocides which may be used according to the invention, mention may be made of nematicides, molluscicides etc. It is possible to apply one or several active materials belonging to the same class of biocides or to a different class.

Thus, as non-limiting examples of preferred active materials, mention may be made inter alia of Ametryne, Diuron, Linuron, Chlortoluron, Isoproturon, Nicosulfuron, Metamitron, Diazinon, Aclonifen, Atrazine, Chlorothalonil, Bromoxynil, Bromoxynil heptanoate, Bromoxynil octanoate, Mancozeb, Maneb, Zineb, Phenmedipham, Propanyl, the phenoxyphenoxy series, the series of heteroaryloxyphenoxy, CMPP, MCPA, 2,4-D, Simazine, active products from the series of imidazolinones, organophosphorus family, with notably Azinphos-ethyl, Azinphos-methyl, Alachlor, Chlorpyriphos, Diclofop-methyl, Fenoxaprop-p-ethyl, Methoxychlor, Cypermethrin, Fenoxycarb, cymoxanil, chlorothalonyl, neonicotinoid insecticides, the family of triazole fungicides such as azaconazole, bromuconazole, ayproconazole, difenoconazole, diniconazole, epoxyconazole, fenbuconazole, flusilazole, myclobutanyl, tebuconazole, triadimefon, triadimenol, strobilurins such as pyraclostrobin, picoxystrobin, azoxystrobin, famoxadone, kresoxym-methyl and trifloxystrobin, sulfonylureas such as bensulfuron-methyl, chlorimuron-ethyl, chlorsulfuron, metsulfuron-methyl, nicosulfuron, sulfomethuron-methyl, triasulfuron, tribenuron-methyl.

Non-water-soluble products are selected from this list.

The following active plant protection products may notably be applied:

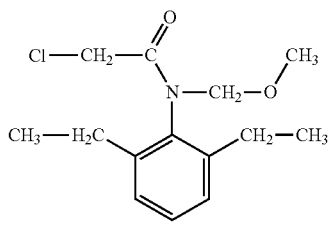

Alachlor

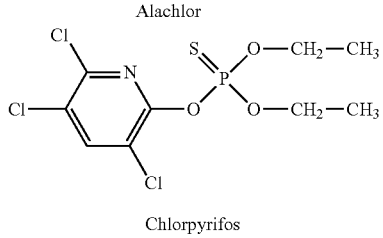

Chlorpyrifos

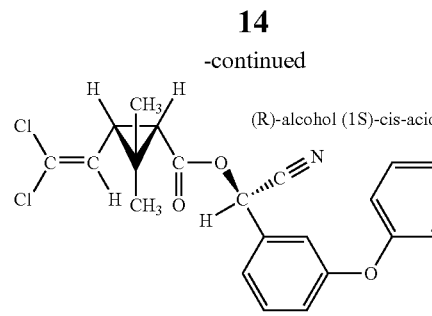

(R)-alcohol (1S)-cis-acid (S)-alcohol (1R)-cis-acid
As a racemic mixture and/or as isolated stereoisomers..
alpha-cypermethrin

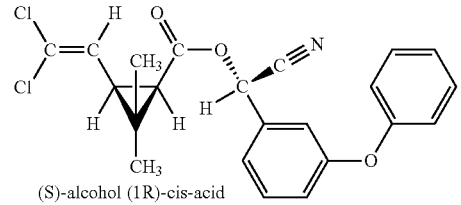

Phenmedipham

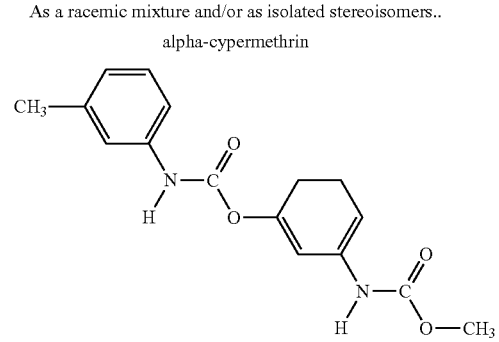

Propanil

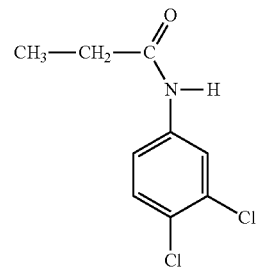

Pendimethalin

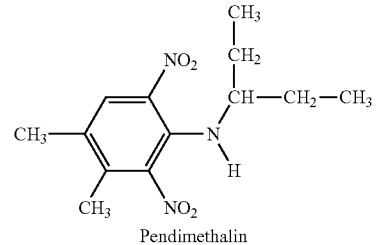

tridimenol

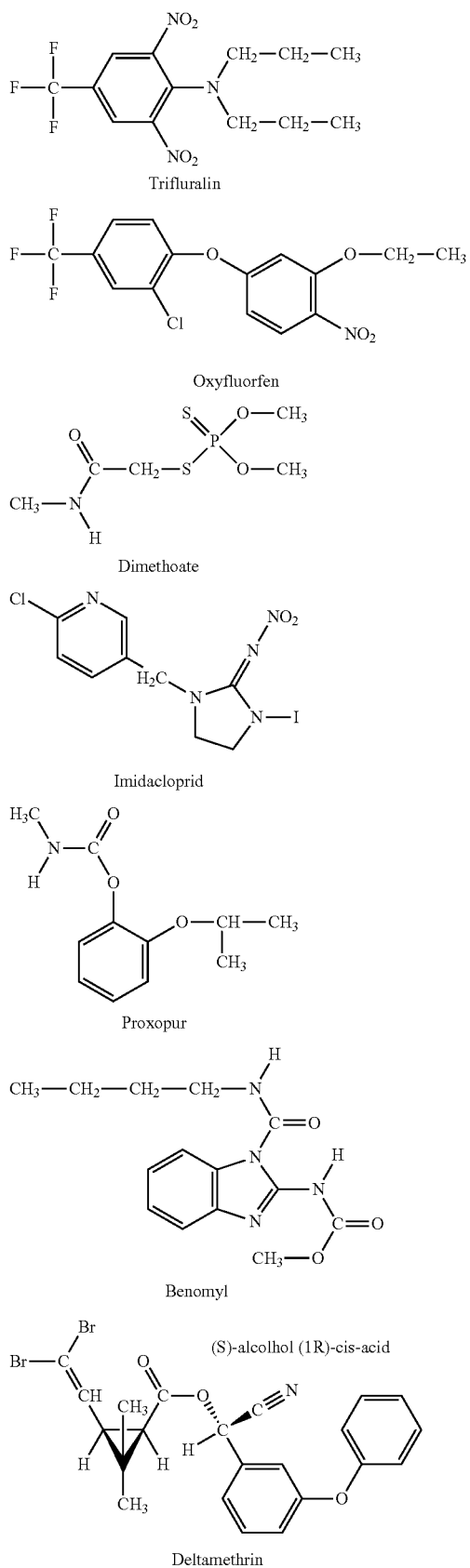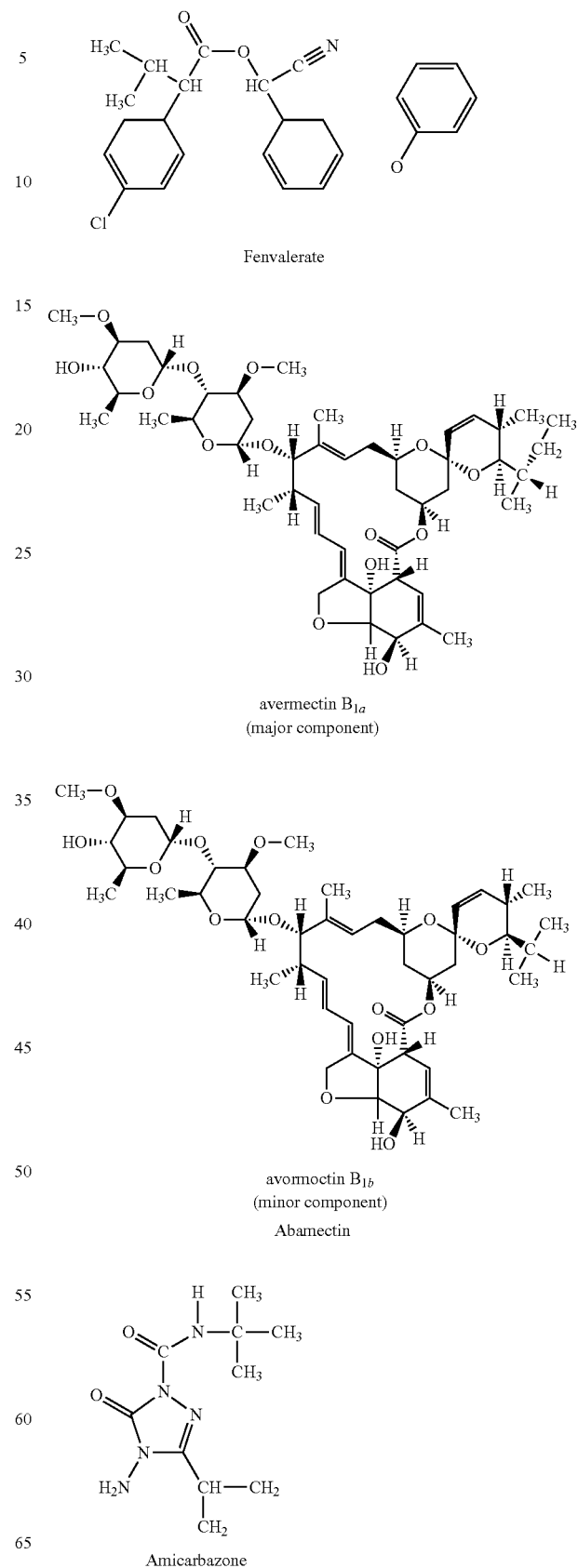

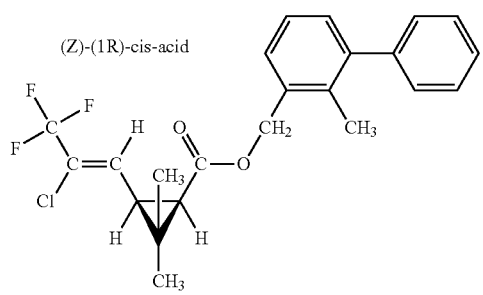
(Z)-(1R)-cis-acid
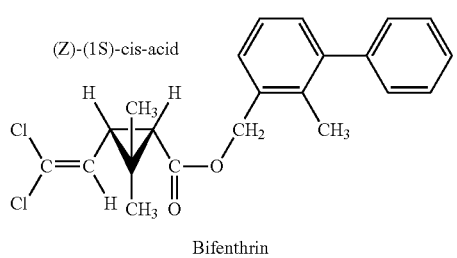
(Z)-(1S)-cis-acid
Bifenthrin
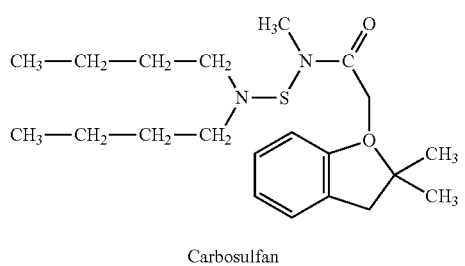
Carbosulfan
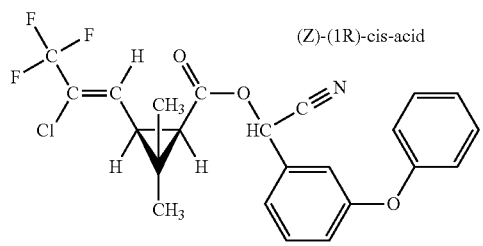
(Z)-(1R)-cis-acid
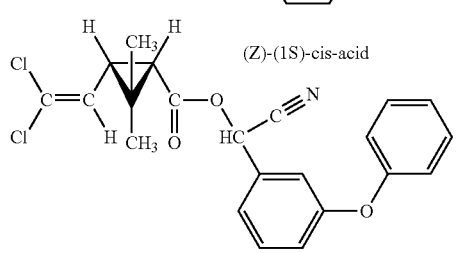
(Z)-(1S)-cis-acid
Cyfluthrin
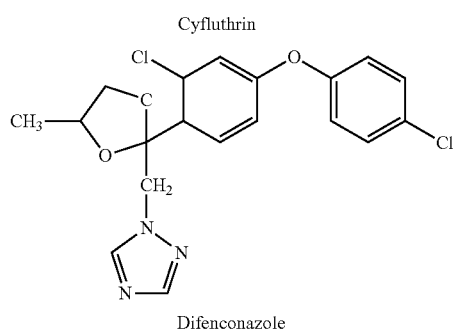
Difenconazole
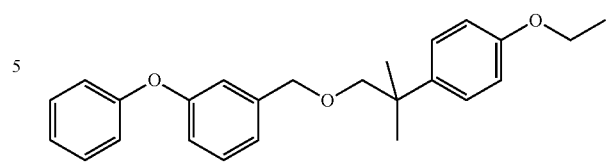
Ethofenprox
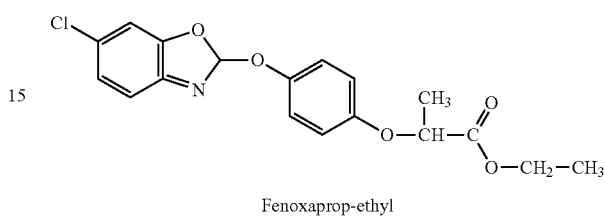
Fenoxaprop-ethyl
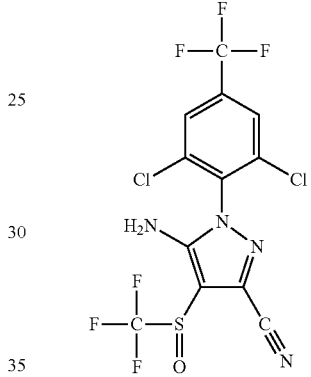
Fipronil
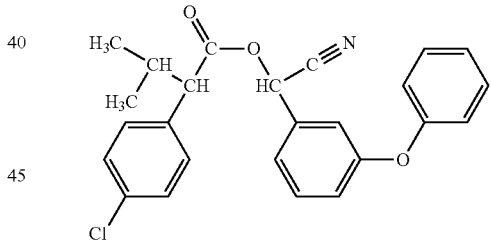
Fenvalerate
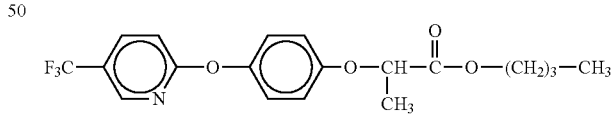
Fluazifop-p-butyl
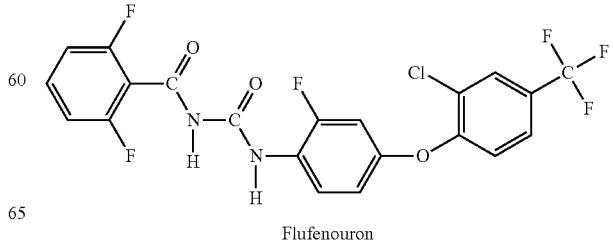
Flufenouron -continued

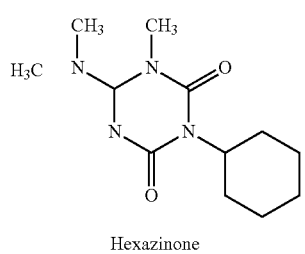
Hexazinone

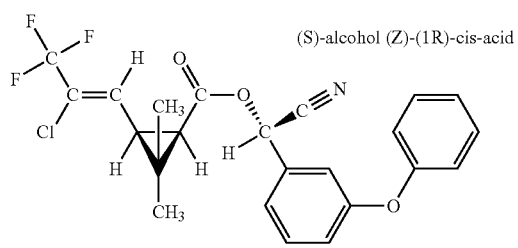
(S)-alcohol (Z)-(1R)-cis-acid

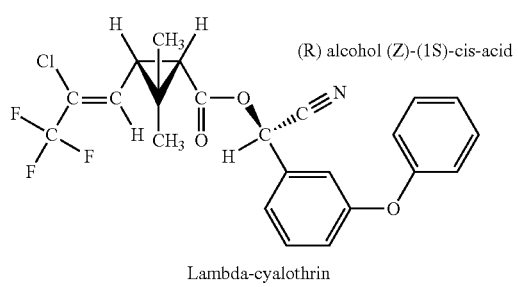
(R) alcohol (Z)-(1S)-cis-acid

Lambda-cyalothrin

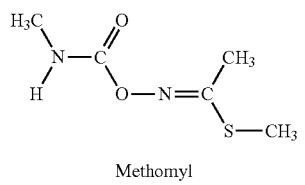
Methomyl

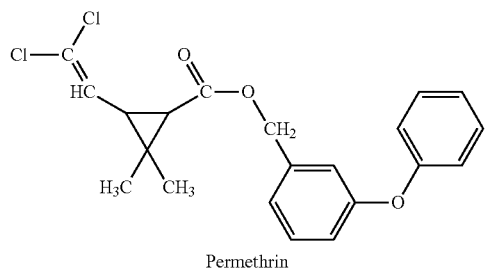
Permethrin

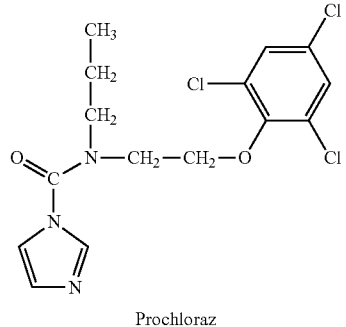
Prochloraz

-continued

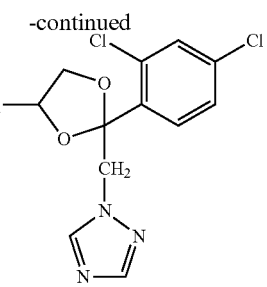
Propiconazole

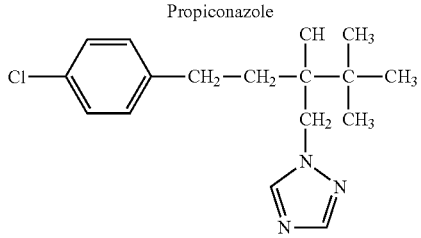
Tebuconazole

These products and designations are known to one skilled in the art. It is possible to combine several active plant protection products.

The plant protection formulation may comprise a surfactant, preferably an emulsifier. Emulsifiers are agents intended to facilitate emulsification after putting the formulation in the presence of water, and/or stabilization (over time and/or in temperature) of the emulsion, for example by avoiding separation of the phases.

The surfactant may be a preferably polyalkoxylated, anionic, non-ionic, cationic, amphoteric (a term also including zwitterionic surfactants) surfactant. This may be a mixture or a combination of these surfactants.

As examples of anionic surfactants, mention may be made without intending to be limited thereto, of:
  alkylsulfonic acids, arylsulfonic acids, optionally substituted with one or several hydrocarbon groups, and the acid function of which is partly or totally salified, like $C_8$-$C_{50}$ alkylsulfonic acids, more particularly $C_8$-$C_{30}$, preferably $C_{10}$-$C_{22}$ alkylsulfonic acids, benzenesulfonic acids, naphthalenesulfonic acids, substituted with one to three $C_1$-$C_{30}$, preferably $C_4$-$C_{16}$ alkyl and/or $C_2$-$C_{30}$, preferably $C_4$-$C_{16}$ alkenyl groups,
  mono- or di-esters of alkylsulfosuccinic acids, including the linear or branched alkyl portion optionally substituted with one or several linear or branched $C_2$-$C_4$ hydroxylated and/or alkoxylated (preferably ethoxylated, propyxylated, ethopropoxylated) groups,
  phosphate esters more particularly selected from those comprising at least one linear or branched, saturated, unsaturated or aromatic hydrocarbon group, comprising 8 to 40 carbon atoms, preferably 10 to 30, optionally substituted with at least one alkoxylated (ethoxylated, propoxylated, ethopropoxylated) group. Further, they comprise at least one phosphate ester group, mono- or di-esterified so that it is possible to have one or two free or partly or totally salified groups. The preferred phosphate esters are of the type of the mono- and di-esters of phosphoric acid and of alkoxylated (ethoxylated and/or propxylated) mono-, di- or tri-styrylphenol or alkoxylated (ethoxylated and/or propoxylated) mono-, di- or trialkylphenol optionally substituted with one to four alkyl groups; of phosphoric acid and of an alkoxylated (ethoxylated or ethopropoxylated) $C_8$-$C_{30}$, preferably $C_{10}$-$C_{22}$ alcohol; of phosphoric acid and of a non-alkoxylated $C_8$-$C_{22}$, preferably $C_{10}$-$C_{22}$ alcohol, sulfate esters obtained from saturated or aromatic alcohols optionally substituted with one or several alkoxylated (ethoxylated, propoxylated, ethopropoxylated) groups, and for which the sulfate functions appear in the free acid form, or are partly or totally neutralized. As an example, mention may be made of sulfate esters more particularly obtained from saturated or unsaturated $C_8$-$C_{20}$ alcohols, which may comprise 1 to 8 alkoxylated (ethoxylated, propoxylated, ethopropoxylated) units; sulfate esters obtained from polyalkoxylated phenol substituted with 1 to 3 saturated or unsaturated $C_2$-$C_{30}$ hydroxycarbon groups, and in which the number of alkoxylated units is comprised between 2 and 40; the sulfate esters obtained from polyalkoxylated mono-, di- or tri-styrylphenol in which the number of alkoxylated units varies from 2 to 40.

The anionic surfactants may be in the acid form (they are potentially anionic), or in a partly or totally salified form with a counter-ion. The counter-ion may be an alkaline metal, such as sodium or potassium, an earth alkaline metal, such as calcium, or further an ammonium ion of formula $N(R)_4^+$ in which the R groups, either identical or different, represent a hydrogen or a $C_1$-$C_4$ alkyl group optionally substituted with an oxygen atom.

As examples of non-ionic surfactants, mention may be made, without intending to be limited thereto:

polyalkoxylated (ethoxylated, propoxylated, ethopropoxylated) phenols substituted with at least one $C_4$-$C_{20}$, preferably $C_4$-$C_{12}$ alkyl group or substituted with at least one alkylaryl group, the alkyl portion of which is a $C_1$-$C_6$ alkyl. More particularly, the total number of alkloxylated units is comprised between 2 and 100. As an example, mention may be made of polyalkoxylated mono-, di- or tri-(phenylethyl)phenols, or polyalkoxylated nonylphenols. Among ethoxylated and/or propoxylated, sulfated and/or phosphated di- or tri-styrylphenols, mention may be made of ethoxylated di-(phenyl-1-ethyl)phenol, containing 10 oxyethylene units, ethoxylated di-(phenyl-1-ethyl)phenol containing 7 oxyethylene units, sulfated ethoxylated di-(phenyl-1-ethyl)phenol containing 7 oxyethylene units, ethoxylated tri-(phenyl-1-ethyl)phenol containing 8 oxyethylene units, ethoxylated tri-(phenyl-1-ethyl)phenol containing 16 oxyethylene units, sulfated ethoxylated tri-(phenyl-1-ethyl)phenol containing 16 oxyethylene units, ethoxylated tri-(phenyl-1-ethyl)phenol containing 20 oxyethylene units, phosphated ethoxylated tri-(phenyl-1-ethyl)phenol containing 16 oxyethylene units.

polyalkoxylated (ethoxylated, propyxylated, ethopropoxylated) $C_6$-$C_{22}$ fatty acids or alcohols. The number of alkoxylated units is comprised between 1 and 60. The ethoxylated fatty acid term includes both products obtained by ethoxylation of a fatty acid by ethylene oxide and those obtained by esterification of a fatty acid by a polyethylene glycol.

polyalkoxylated (ethoxylated, propoxylated, ethopropoxylated) triglycerides of vegetable or animal origin. Thus, triglycerides from lard, tallow, ground nut oil, butter oil, cotton seed oil, flax oil, olive oil, palm oil, grapeseed oil, fish oil, soya bean oil, castor oil, rapeseed oil, coprah oil, coconut oil, and comprising a total number of alkoxylated units comprised between 1 and 60. The ethoxylated triglyceride term is directed both at products obtained by ethoxylation of a triglyceride with ethylene oxide and those obtained by transesterification of a triglyceride with a polyethylene glycol.

sorbitan esters, optionally polyalkoxylated (ethoxylated, propoxylated, ethopropoxylated), more particularly the esters of cyclized sorbitol and of $C_{10}$-$C_{20}$ fatty acids such as lauric acid, stearic acid, or oleic acid, and comprising a total number of alkoxylated units comprised between 2 and 50.

Useful emulsifiers are notably the following products, all marketed by Rhodia:

Soprophor® TSP/724: a surfactant based on ethopropoxylated tristyrylphenol,

Soprophor® 796/P: surfactant based on ethopropoxylated tristyrylphenol

Soprophor® CY 8: surfactant based on ethoxylated tristyrylphenol

Soprophor® BSU: surfactant based on ethoxylated tristyrylphenol

Alkamuls® RC: surfactant based on ethoxylated castor oil

Alkamuls® OR/36: surfactant based on ethoxylated castor oil

Alkamuls® T/20: surfactant based on ethoxylated sorbitan ester.

The formulation advantageously comprises at least 2%, preferably at least 5%, preferably at least 8%, by weight of dry material of at least one surfactant d).

It is mentioned that the solvent may be associated with an aromatic and/or non-aromatic surfactant.

The concentrated plant protection formulation preferably does not contain large amounts of water. Typically the water content is less than 50% by weight, advantageously less than 25% by weight. It will generally be less than 10% by weight.

The formulation is preferably a liquid formulation, for example in the form of an emulsifiable concentrate (EC), a concentrated emulsion (EW), a soluble concentrate (SL), a suspo-emulsion (SE) or a microemulsion (AE). In this case, it preferably comprises less than 500 g/L of water, more preferably less than 250 g/L. It will generally be less than 100 g/L.

The formulations may advantageously comprise:

a) from 0.01% to 60%, preferably from 10% to 50%, of the plant protection product, by weight of active material, b) from 10% to 92%, preferably from 20% to 80%, of the esteramide compound of formula (I) according to the present invention, by weight, c) from 1 to XX %, preferably from XX to XX % by weight of at least one co-solvent or another solvent, d) from 2% to 60%, preferably from 5% to 50%, preferably from 8% to 25%, by weight of dry material of an emulsifier, preferably a surfactant, e) from 0 to 20% by weight of water.

Producing solid formulations is not excluded, for example formulations, in which a liquid comprising the plant protection product solubilized in the solvent, is supported by a mineral and/or dispersed in a solid matrix.

The formulation may of course comprise other ingredients (or "other additives") than the active plant protection product, solvent(s), optional emulsifier(s) and optional water. It may notably comprise viscosity modifiers, anti-foam agents, notably silicone anti-foam agents, anti-bounce agents, anti-leaching agents, inert fillers, notably mineral fillers, antifreeze agents, stabilizers, coloring agents, emetic agents, stickers (adhesion promoters).

Notably the formulations may comprise co-solvents and other solvents c). The formulations comprise such other solvents in particular when the esteramide of formula I according to the invention is used as a co-solvent.

The other solvents or co-solvents c) are preferentially selected from the following group:
- linear or branched, saturated or unsaturated, aliphatic hydrocarbons optionally comprising a halogen, phosphorus, sulfur and/or nitrogen atom and/or a functional group,
- saturated, unsaturated or aromatic carbocyclic or heterocyclic hydrocarbons optionally comprising a halogen, phosphorus, sulfur and/or nitrogen atom and/or a functional group.

Still more advantageously, they are selected in the following group:
- alkanes, cycloalkanes and aromatic derivatives, for example paraffins with a linear or branched chain such as <<white oil>> or decalin; mono- di- or tri-alkyl benzenes or naphthalenes, compounds marketed under the name of Solvesso 100, 150, 200 standard and grades ND;
- aliphatic, cycloaliphatic or aromatic mono-, di- or tri-esters, for example alkyl alkanoate such as methyl oleate, benzyl alkanoates; alkyl benzoates; gamma butyrolactone; caprolactone; esters of glycerol and citric acid; alkyl salicylates; phthalates; dibenzoates; acetoacetates; glycol ether acetates, dipropylene glycol diacetate;
- alkyl mono- di- or tri-phosphates such as for example triethyl phosphate; tributyl phosphate; or tri-2-ethylhexylphosphate;
- aliphatic, cycloaliphatic or aromatic ketones such as dialkyl ketones, benzyl ketones; fenchone; actetophenone; cyclohexanone; alkyl cyclohexanones;
- aliphatic, cycloaliphatic or aromatic alcohols such as for example glycols, 2-ethylhexanol; cyclohexanol; benzyl alcohols; tetrahydrofurfuryl alcohol;
- aliphatic, cycloaliphatic or aromatic ethers such as ethers of glycol, notably of ethylene and propylene glycol, and their polymers, diphenyl ether, dipropylene glycol; monomethyl or monobutyl ether, monobutyl ether of tripropylene glycol; alkoxyalkanols; dimethyl isosorbide;
- fatty acids such as for example linoleic acid, linolenic acid, oleic acid;
- carbonates such as for example propylene or butylene carbonate; lactates; fumarates, succinates, adipates, maleates;
- amides such as for example alkyldimethylamides, dimethyl-decanoamide;
- alkyl ureas;
- amines such as for example alkanolamines, morpholine; N-alkyl-pyrrolidones;
- tetramethyl sulfone;
- dimethyl sulfoxide;
- halogenoalkanes or halogenated aromatic solvents such as for example chloroalkanes or chlorobenzene.

Other particularly preferred solvents are alkylbenzenes and naphthalenes, compounds marketed under the name of Solvesso 100, 150, 200 standard and grades ND, alkanolamides and their alkyl ethers, fatty acids and their alkyl esters such as for example methyl oleate, alkyldimethylamides, N-alkyl-pyrrolidones, tri-alkylphosphates, aliphatic (linear or branched) alcohols and their esters, di-basic esters, paraffins (linear or branched) such as <<white oil>>, glycols and glycol ethers, acetophenone.

Crystallization inhibitors may also be present in the formulations. These are the solvents mentioned above. These may also be non-polyalkoxylated fatty alcohols or fatty acids, for example mention is made of the product Alkamuls® OL700 marketed by Rhodia, alkanolamides, polymers etc., Standard methods for preparing plant protection formulations or mixtures of solvents may be applied. It is possible to operate by simply mixing the constituents.

The concentrated plant protection formulation is generally intended to be spread out on a cultivated field or a field to be cultivated, for example a soya field, most often after dilution with water, in order to obtain a diluted composition. Dilution is generally achieved by the farmer, directly in a tank ("tank-mix"), for example in the tank of a device intended to spread out the composition. It is not excluded that the farmer add other plant protective products, for example fungicides, herbicides, pesticides, insecticides, fertilizers, adjuvants . . . . Thus, the formulation may be used for preparing a composition diluted in water of the active plant protection product, by mixing at least one portion by weight of concentrated formulation with at least 10 portions of water, preferably less than 10,000 portions. The dilution levels and the amounts to be applied on the field generally depend on the plant protection product and on the desirable dose for treating the field (this may be determined by the farmer).

The examples which follow illustrate the invention without however limiting it.

EXAMPLES

The preparation of the compounds of the invention is described in Examples 3 and 4.

The compounds of Examples 1 and 2 are synthesis intermediates of the compounds of Examples 3 and 4.

Example 1C (Comparative)

Preparation of compound 1, (methyl 2-(dimethylamino)-2-oxoacetate)

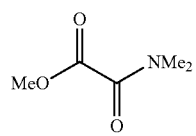

In a 1,000 mL reactor are added at 0° C., 360 g (4 mol) of dimethylamine (DMA) solution at 50% by weight in methanol and 43.2 g (0.2 mol) of sodium methylate at 25% by weight in methanol. To this mixture are added at 0-5° C. and within 1 hour, 472 g (4 mol) of dimethyl oxalate. The mixture is maintained with stirring and at 0° C. for 2 hours. The reaction medium is concentrated in vacuo ($P_{max}$=200 mbars) for removing residual DMA and methanol and an 85% orthophosphoric acid solution (23 g 0.2 mol) is then added. The salts formed are filtered and then the filtrate is distilled in vacuo ($T_{bp}$=68-70° C., P<1 mbar) in order to recover the desired product (461 g).

Example 2C (Comparative)

Preparation of compound 2, (ethyl 2-(dimethylamino)-2-oxoacetate)

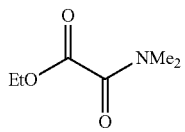

In a 1,500 mL reactor, are added at 0° C., 360 g (4 mol) of dimethylamine (DMA) solution at 50% by weight in methanol and 44 g (0.2 mol) of sodium methylate at 25% by weight in methanol. To this mixture are added at 0-5° C. and within 1 hour, 584 g (4 mol) of diethyl oxalate. The mixture is maintained with stirring at 0° C. for 4 hours. The reaction medium is concentrated in vacuo (Pmax=200 mbars) for removing residual DMA and methanol and an 85% orthophosphoric acid solution (23.3 g 0.2 mol) is then added. The salts formed are filtered and the filtrate is then distilled in vacuo ($T_{bp}$=77-78° C., P<1 mbar) for recovering the desired product (500 g).

Example 3

Preparation of compound 3, (2-ethyl-hexyl 2-(dimethylamino)-2-oxoacetate)

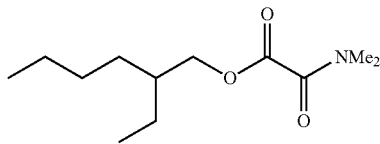 [SMILES: CCCCC(CC)COC(=O)C(=O)N(C)C]

Operating Procedure with Acid Catalysis

In a 1,000 mL reactor, are mixed at 20-25° C., methyl 2-(dimethylamino)-2-oxoacetate (compound 1) (390 g, 2.98 mol), 2-ethyl-hexan-1-ol (464 g, 3.5 mol) and 98% sulfuric acid (66 g, 0.67 mol). The temperature of the mixture is brought to and maintained at 80° C. for 24 hours. The progression of the reaction is tracked by gas chromatography analysis. At the end of the reaction, the methanol formed is removed from the reaction medium by distillation under reduced vacuum (Pmin=150 mbars) and an aqueous solution of sodium hydrogencarbonate is then added to the reaction medium so that the final pH is 7. The organic phase is separated from the aqueous phase. The latter is counter-extracted with 500 mL of dichloromethane. The organic phases are collected and then the reaction medium is concentrated in order to remove the dichloromethane. To the residue, are added 5 g of potassium carbonate and the thereby obtained medium is then distilled under partial vacuum ($T_{bp}$ 150° C., P<1 mbar). The expected product is obtained with a purity of more than 98% (578 g).

Example 4

Preparation of compound 4, (n-decyl 2-(dimethylamino)-2-oxoacetate)

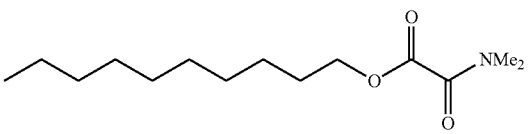 [SMILES: CCCCCCCCCCOC(=O)C(=O)N(C)C]

Operating Procedure with Basic Catalysis

In a 250 mL reactor, are mixed at 20-25° C., n-decan-1-ol (114 g, 0.72 mol) and sodium (2.8 g, 0.12 mol). The temperature of the mixture is brought to and maintained at 50° C. for 8 hours, until total disappearance of the solid. After returning the temperature of the reaction medium to 20° C., methyl 2-(dimethylamino)-2-oxoacetate (compound 1) (79 g, 0.6 mol) is added and the reaction medium is maintained with stirring at 25° C. for 5 hours. The progression of the reaction is tracked by gas chromatography analysis. At the end of the reaction, a 4N sulfuric acid solution (10 mL) is added at 25° C. The salts formed are removed by filtration. The organic phase is separated from the aqueous phase. The latter is counter-extracted with 50 mL of dichloromethane. The organic phases are collected and the reaction medium is then concentrated for removing the dichloromethane. To the residue are added 5 g of potassium carbonate and the thereby obtained medium is distilled under partial vacuum ($T_{bp}$ 150° C., P<1 mbar). The expected product is obtained with a purity of more than 98% (55 g).

Operating Procedure with Acid Catalysis

In a 1,500 mL reactor, are mixed at 20-25° C., methyl 2-(dimethylamino)-2-oxoacetate (compound 1) (398 g 3 mol), n-decan-1-ol (567 g, 3.6 mol) and 98% sulfuric acid (59 g 0.6 mol). The temperature of the mixture is brought to and maintained at 120° C. for 24 hours. Progression of the reaction is tracked by gas chromatography analysis. At the end of the reaction, the methanol formed is removed from the reaction medium by distillation under reduced vacuum (P min=150 mbars) and an aqueous solution of sodium hydrogen carbonate is then added to the reaction medium so that the final pH is 7. The organic phase is separated from the aqueous phase. The latter is counter-extracted with 500 mL of dichloromethane. The organic phases are collected and the reaction medium is then concentrated for removing the dichloromethane. To the residue, are added 5 g of potassium carbonate and the thereby obtained medium is then distilled under partial vacuum ($T_{bp}$ 150° C., P<1 mbar). The expected product is obtained with purity of more than 98% (633 g).

Example 5

Preparation of compound 5, (cyclohexyl 2-(dimethylamino)-2-oxoacetate)

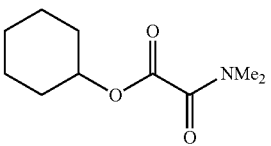 [SMILES: CN(C)C(=O)C(=O)OC1CCCCC1]

Operating Procedure with Acid Catalysis

In a 1,000 mL reactor, are mixed at 20-25° C., methyl 2-(dimethylamino)-2-oxoacetate) (compound 1) (393 g, 3 mol), cyclohexanol (360 g, 3.6 mol) and 98% sulfuric acid (66 g, 0.67 mol). The temperature of the mixture is brought to and maintained at 80° C. for 36 hours. Progression of the reaction is followed by gas chromatography analysis. At the end of the reaction, the methanol formed is removed from the reaction medium by distillation under reduced vacuum (P min=150 mbars) and an aqueous solution of sodium hydrogen carbonate is then added to the reaction medium so that the final pH is 7. The organic phase is separated from the aqueous phase. The latter is counter-extracted with 500 mL of dichloromethane. The organic phases are collected and the reaction medium is then concentrated for removing the dichloromethane. To the residue are added 5 g of potassium carbonate and the thereby obtained medium is then distilled under partial vacuum ($T_{bp}$ 115-120° C., P<1 mbar). The expected product is obtained with a purity of more than 98.2% (466 g).

Measurement of Solubility of the Solvent in Water

In a glass flask, a specific weight of compound is weighed. A known mass of water is added on to this compound. This mixture is magnetically stirred at a temperature of +20° C. for 2 hours. After this period, if visually, the solution has cloudiness or heterogeneity, a new mass of water is added to the mixture. This iteration occurs until a limpid solution is obtained. Maximum solubility is then less than the last value having led to a cloudy or heterogeneous mixture and greater than that having led to a limpid mixture.

| Compounds | Solubility in water (wt %) |
| --- | --- |
| 1C | 5 < S < 10 |
| 2C | 1 < S < 5 |
| 3 | <0.1 |
| 4 | <0.025 |

The water solubility of the compounds according to the invention is at least 10 times less and up to 400 times less than that of the comparative examples.

Solubility of Certain Agrochemical Actives in Solvents

The following tests were conducted:
Formulations were made by diluting various actives, reported below in the table, in the compounds 1C, 2C, 3 and 4 synthesized above.
1) Visual observation at 25° C.
The aspect of the formulation is noted and the presence of crystals is possibly located.
2) Visual observation at 0° C.
The formulation is placed at 0° C. for 7 days and the aspect of the formulation is noted and the presence of crystals is possibly located (CIPAC MT39 test).
3) Visual observation at 0° C. with nucleation (by introducing a crystal of the pure active into the liquid)
A crystal of the active material is introduced into the formulation which has spent 7 days at 0° C. for nucleation, and the formulation is again placed for 7 days at 0° C. The aspect of the formulation is noted and the presence of crystals or the growth of the introduced crystal is possibly located.
The actives used are commercially available. When the formation of active crystals is observed, the term of <<crystal>> is indicated in the table below. In this case, the following test is not conducted and the symbol <<->> is indicated in the table. When the solution remains limpid (absence of solid or cloudiness), it is the term of <<limpid>> which is indicated in the table of results below.

The results are recorded in the following table:

TABLE (I)

| Solvent | Active | Aspect at 25° C. | Aspect at 0° C. | Aspect at 0° C. with nucleation |
| --- | --- | --- | --- | --- |
| Compound 1 | Alachlor 48% EC | Limpid | Limpid | Limpid |
| | alpha-Cypermethrin 10% EC | Limpid | Limpid | Limpid |
| | Phenmedipham 16% EC | Limpid | Limpid | Limpid |
| | Propanil 36% EC | Limpid | Limpid | Limpid |
| | Pendimethalin 33% EC | Limpid | Crystal | — |
| | Tebuconazole 25% EC | Limpid | Crystal | — |
| | Trifluralin 40% EC | Limpid | Crystal | — |
| | Difenconazole 25% EC | Limpid | Limpid | Limpid |
| | Dimethoate 40% EC | Limpid | Crystal | — |
| | Oxyfluorfen 22% EC | Limpid | Crystal | — |
| | Propuxur 20% EC | Limpid | Limpid | Limpid |
| | Azoxystrobin 25% EC | Limpid | Crystal | — |
| Compound 2 | Alachlor 48% EC | Limpid | Limpid | Limpid |
| | Chlorpyrifos 40% EC | Limpid | Limpid | Limpid |
| | alpha-Cypermethrin 10% EC | Limpid | Limpid | Limpid |
| | Phenmedipham 16% EC | Limpid | Limpid | Limpid |
| | Propanil 36% EC | Limpid | Limpid | Limpid |
| | Pendimethalin 33% EC | Limpid | Crystal | — |
| | Tebuconazole 25% EC | Limpid | Crystal | — |
| | Trifluralin 40% EC | Limpid | Limpid | Limpid |
| | Difenconazole 25% EC | Limpid | Limpid | Limpid |
| | Dimethoate 40% EC | Limpid | Limpid | Crystal |
| | Oxyfluorfen 22% EC | Limpid | Limpid | Limpid |
| | Propuxur 20% EC | Limpid | Crystal | — |
| | Azoxystrobin 25% EC | Limpid | Crystal | — |
| Compound 3 | Alachlor 48% EC | Limpid | Limpid | Limpid |
| | Chlorpyrifos 40% EC | Limpid | Limpid | Limpid |
| | alpha-Cypermethrin 10% EC | Limpid | Limpid | Limpid |
| | Propanil 36% EC | Limpid | Limpid | Limpid |
| | Pendimethalin 33% EC | Limpid | Crystal | — |
| | Trifluralin 40% EC | Limpid | Limpid | Limpid |
| | Difenconazole 25% EC | Limpid | Limpid | Limpid |
| | Dimethoate 40% EC | Limpid | Crystal | — |
| | Oxyfluorfen 22% EC | Limpid | Limpid | Crystal |
| | Propuxur 20% EC | Limpid | Crystal | — |
| Compound 4 | Alachlor 48% EC | Limpid | Limpid | Limpid |
| | Chlorpyrifos 40% EC | Limpid | Crystal | — |
| | Propanil 36% EC | Limpid | Limpid | Limpid |
| | Trifluralin 40% EC | Limpid | Crystal | — |
| | Difenconazole 25% EC | Limpid | Limpid | Limpid |
| | Oxyfluorfen 22% EC | Limpid | Limpid | Limpid |

It is clearly seen from the table above that the compounds according to the invention are good solvents for most of agrochemical actives.

As this property is coupled with their low water solubility, the compounds according to the invention thus have good capability of forming emulsifiable concentrates of plant protection actives.

The invention claimed is:

1. An esteramide compound of formula (I'):

wherein:
- A is a covalent bond or a methylene group —$CH_2$—;
- $R^1$ is an optionally substituted, linear or branched, saturated or unsaturated acyclic aliphatic group, or optionally substituted, saturated or unsaturated carbocyclic group comprising from 5 to 36 carbon atoms.

2. The compound as defined by claim 1, wherein $R^1$ is a linear or branched, optionally substituted, alkyl group, comprising from 5 to 36 carbon atoms.

3. The compound as defined by claim 1, wherein $R^1$ is a linear or branched, optionally substituted, alkyl group, comprising from 5 to 15 carbon atoms.

4. The compound as defined by claim 1, wherein A represents a covalent bond.

5. The compound as defined by claim 1, wherein $R^1$ is selected from the group consisting of n-pentyl, isopentyl, sec-pentyl, n-hexyl, isohexyl, sec-hexyl, methylcyclohexyl, 2-ethylbutyl, 3-methylpentyl, n-heptyl, isoheptyl, sec-heptyl, 3-methylhexyl, 4-methylhexyl, 1-ethylpentyl, 2-ethylpentyl, 3-ethylpentyl, n-octyl, isooctyl, 3-methylheptyl, n-nonyl, n-decyl, undecyl, n-dodecyl, tridecyl, tetradecyl and a pentadecyl group.

6. The compound as defined by claim 1, wherein the compound is selected from the group consisting of:

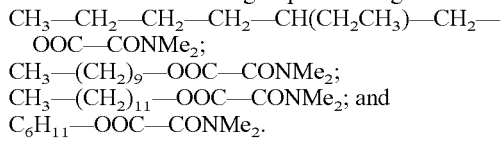

7. A method for preparing an esteramide compound, the method comprising the following steps:
  a) reacting a compound of formula (II) ROOC-A-COOR, R being a methyl group or an ethyl group, with an amine of formula $HNMe_2$, in the presence of a basic catalyst, in order to obtain a compound of formula (III'): ROOC-A-$CONMe_2$; and
  b) reacting the compound of the aforementioned formula (III') with an alcohol of formula $R^1OH$, wherein $R^1$ is defined wherein the resulting esteramide compound has a formula (I'), as defined in claim 1.

8. A method for preparing an esteramide compound as defined by claim 1, the method comprising the following steps:
  a') reacting a compound of formula (II) ROOC-A-COOR, R being a methyl group or an ethyl group, with an alcohol of formula $R^1OH$, wherein $R^1$ is defined by claim 1, in the presence of a catalyst, in order to obtain a mixture comprised of a compound of formula (IV'): $R^1$OOC-A-COOR and a compound of formula (V'): $R^1$OOC-A-COOR$^1$; and
  b') reacting the aforementioned mixture as obtained in the preceding step a') with an amine of formula $HNMe_2$, in the presence of a basic catalyst, wherein the resulting esteramide compound has a formula (I') as defined in claim 1.

9. A method for preparing an esteramide compound, the method comprising the following steps:
  a") reacting a compound of formula (II) ROOC-A-COOR, R being a hydrogen, or a methyl group or an ethyl group, with an alcohol of formula $R^1OH$, wherein $R^1$ is defined by claim 1, in the presence of an acid catalyst, in order to obtain a mixture comprised of a compound of formula (IV'): $R^1$OOC-A-COOR and a compound of a formula (V'): $R^1$OOC-A-COOR$^1$; and
  b") reacting the aforementioned mixture as obtained in the preceding step a') with an amine of formula $HNMe_2$, in the presence of a basic catalyst, wherein the resulting esteramide compound has a formula (I'), as defined in claim 1.

10. A method of using the compound of formula (I') as defined by claim 1, the method comprising using an effective amount of the compound of formula (I') in a solvent, a co-solvent, a coalescence agent, a crystallization inhibitor, or a plasticizer.

11. A plant protection formulation, comprising a compound of formula (I') as defined by claim 1, in combination with an active product.

12. A coalescence agent comprising a compound of formula (I') as defined by claim 1.

13. A crystallization inhibitor comprising a compound of formula (I') as defined by claim 1.

14. A formulation comprising a compound of formula (I') as defined by claim 1.

15. The formulation of claim 14, wherein the formulation is formulated for cleaning, for stripping, for degreasing, for coating, for solubilisation of resins, for cleaning photoresists, or for cleaning liquid crystal screens.

16. A lubricant formulation comprising a compound of formula (I') as defined by claim 1.

17. A pigment or ink formulation comprising a compound of formula (I') as defined by claim 1.

* * * * *